United States Patent
Ryu et al.

(10) Patent No.: US 6,239,076 B1
(45) Date of Patent: May 29, 2001

(54) HERBICIDAL 2-(5-ISOXAZOLINYL METHYLOXYPHENYL)-4,5,6,7-TETRAHYDRO-2H-INDAZOLE DERIVATIVES

(75) Inventors: Eung Kul Ryu; Dong Ju Jeon, both of Taejon-si; Jong Hwan Song, Chungcheongbukdo; Hyoung Rae Kim, Taejon-si; Jung No Lee, Chungcheongnamdo; Kyoung Mahn Kim; Kwang Yun Cho, both of Taejon-si, all of (KR)

(73) Assignee: Korea Research Institute of Chemical Technology, Taejon-si (KR)

( * ) Notice: Subject to any disclaimer, the term of this patent is extended or adjusted under 35 U.S.C. 154(b) by 0 days.

(21) Appl. No.: 09/647,902

(22) PCT Filed: Feb. 24, 2000

(86) PCT No.: PCT/KR00/00152

§ 371 Date: Oct. 6, 2000

§ 102(e) Date: Oct. 6, 2000

(87) PCT Pub. No.: WO00/50407

PCT Pub. Date: Aug. 31, 2000

(30) Foreign Application Priority Data

Feb. 25, 1999 (KR) .................................................. 99-6209

(51) Int. Cl.⁷ .................... A61K 31/42; C07D 413/10; A61N 43/80
(52) U.S. Cl. ...................... 504/271; 514/378; 548/240
(58) Field of Search ........................... 548/240; 514/378; 504/271

(56) References Cited

U.S. PATENT DOCUMENTS

| 4,059,434 | 11/1977 | Wolf | 71/92 |
|---|---|---|---|
| 4,124,374 | 11/1978 | Wolf | 71/92 |

FOREIGN PATENT DOCUMENTS

| 2127410A | * 4/1984 | (GB) . |
|---|---|---|
| 60-252465 | 12/1985 | (JP) . |

* cited by examiner

Primary Examiner—Deborah C. Lambkin
Assistant Examiner—Andrea M. D'Souza
(74) Attorney, Agent, or Firm—Bachman & LaPointe, P.C.

(57) ABSTRACT

The present invention relates to 2-(5-isoxazolinylmethyloxyphenyl)-4,5,6,7-tetrahydro-2H-indazole derivatives of formula 1, their preparation method and their use as herbicides. As the compounds have excellent herbicidal activity against paddy weeds comprising ECHOR, SCPJU, MOOVA, CYPSE and SAGPY, and better selectivity, the compounds of the present invention are typically useful as herbicides for control of paddy weeds in conditions with seeded rice and transferred rice.

7 Claims, No Drawings

HERBICIDAL 2-(5-ISOXAZOLINYL METHYLOXYPHENYL)-4,5,6,7-TETRAHYDRO -2H-INDAZOLE DERIVATIVES

This application is a 371 of PCT/KR00/00152 Feb. 24, 2000.

FIELD OF THE INVENTION

The present invention relates to novel 2-(5-isoxazolinylmethyloxyphenyl)-4,5,6,7-tetrahydro-2H-indazole derivatives of the following formula 1, their preparation method and their use as herbicides.

Formula 1

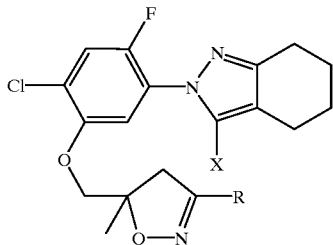

(I)

In the foregoing formula 1,

X represents a chlorine atom or a hydroxy group;

R represents an alkyl group of $C_1$–$C_5$, a substituted or unsubstituted phenyl group, a cyano group, a carboxyl group, a carboxyl ester group, or a substituted or unsubstituted heterocyclic ring; and in case of a phenyl group or a heterocyclic ring being substituted, the phenyl group or the heterocyclic ring is optionally substituted by one or more identical or different substituents selected from the group consisting of alkyl groups of $C_1$–$C_3$, alkoxy groups of $C_1$–$C_3$, halogen atoms, cyano groups, nitro groups, carboxyl groups and carboxyl ester groups.

The compounds of the formula 1 have chiral centers and they can exist as enantiomers. All these separate individual isomers and their racemic mixtures are in the scope of the present invention.

DESCRIPTION OF THE RELATED ART

Some compounds containing an indazole group have been known to be useful for herbicides in the art. For example, U.S. Pat. No. 4,059,434, U.S. Pat. No. 4,124,374 and GB Pat. No. 2,127,410 A disclose 3-chloro-2-(4-chloro-2-fluorophenyl)-4,5,6,7-tetrahydro-2H-indazole, 3-chloro-2-(2,4-dichloro-5-methoxyphenyl)-4,5,6,7-tetrahydro-2H-indazole, 3-methyl-2-(4-chloro-2-fluorophenyl)-4,5,6,7-tetrahydro-2H-indazole, 3-chloro-2-(4-chloro-5-propargyloxy-2-fluorophenyl)-4,5,6,7-tetrahydro-2H-indazole, etc. However, there has been a need for development in the herbicidal activity and selectivity.

We, the inventors of the present invention, have investigated the optimum structures of indazole derivatives in order to develop the herbicides for inhibiting growth of undesirable plants selectively in an established crop, and have synthesized the compounds of the formula 1 which has not been ever developed as a herbicide and have the improved herbicidal activity and selectivity.

SUMMARY OF THE INVENTION

The objective of the present invention is to provide novel 2-(5-isoxazolinylmethyloxyphenyl)-4,5,6,7-tetrahydro-2H-indazole derivatives of the formula 1.

Another objective of the present invention is to provide a preparation method of the said 2-(5-isoxazolinylmethyloxyphenyl)-4,5,6,7-tetrahydro-2H-indazole derivatives.

The further objective of the present invention is to provide herbicidal compositions comprising the said 2-(5-isoxazolinylmethyloxyphenyl)-4,5,6,7-tetrahydro-2H-indazole derivatives as an active ingredient.

The herbicidal compositions according to the present invention have a strong herbicidal activity against paddy weeds comprising ECHOR (*Echinochloa crus-galli* var. oryzicola; common name is barnyardgrass), SCPJU (*Scirpus juncoides* ROXB.; common name is bulrush), MOOVA (*Monochoria vaginalis* PRESL.; common name is monochoria), CYPSE (*Cyperus serotinus* ROTTB.; common name is flat-sedge), and SAGPY (*Sagittaria pygmaea* MIQ.; common name is arrow head) in rice.

DETAILED DESCRIPTION OF THE INVENTION

The present invention relates to 2-(5-isoxazolinylmethyloxyphenyl)-4,5,6,7-tetrahydro-2H-indazole derivatives of the following formula 1.

Formula 1

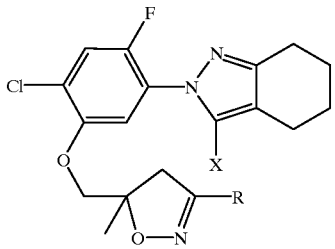

(I)

In the foregoing formula 1,

X represents a chlorine atom or a hydroxy group;

R represents an alkyl group of $C_1$–$C_5$, a substituted or unsubstituted phenyl group, a cyano group, a carboxyl group, a carboxyl ester group, or a substituted or unsubstituted heterocyclic ring; and in case of a phenyl group or a heterocyclic ring being substituted, the phenyl group or the heterocyclic ring is optionally substituted by one or more identical or different substituents selected from the group consisting of alkyl groups of $C_1$–$C_3$, alkoxy groups of $C_1$–$C_3$, halogen atoms, cyano groups, nitro groups, carboxyl groups and carboxyl ester groups.

The compounds of the formula 1 have chiral centers and they can be exist enantiomers. All these separate individual isomers and their racemic mixtures are in the scope of the present invention.

In the formula 1, preferably X is a chlorine atom. And R is preferably a substituted or unsubstituted phenyl group, a substituted or unsubstituted heterocyclic ring or a cyano group.

The representative compounds of the present invention of the formula 1 are as followings:

1) 3-chloro-2-[4-chloro-5-(3-phenyl-5-methylisoxazolin-5-yl)methyloxy-2-fluorophenyl]-4,5,6,7-tetrahydro-2H-indazole (compound No. 1);
2) 3-chloro-2-[4-chloro-5-(3-(4-cyanophenyl)-5-methylisoxazolin-5-yl)methyloxy-2-fluorophenyl]-4,5,6,7-tetrahydro-2H-indazole (compound No. 2);

3) 3-chloro-2-[4-chloro-5-(3-(4-methylphenyl)-5-methylisoxazolin-5-yl)methyloxy-2-fluorophenyl]-4,5,6,7-tetrahydro-2H-indazole (compound No. 3);

4) 3-chloro-2-[4-chloro-5-(3-(2-fluorophenyl)-5-methylisoxazolin-5-yl)methyloxy-2-fluorophenyl]-4,5,6,7-tetrahydro-2H-indazole (compound No. 4);

5) 3-chloro-2-[4-chloro-5-(3-(2,4-dichlorophenyl)-5-methylisoxazolin-5-yl)methyloxy-2-fluorophenyl]-4,5,6,7-tetrahydro-2H-indazole (compound No. 5);

6) 3-chloro-2-[4-chloro-5-(3-(2-nitrophenyl)-5-methylisoxazolin-5-yl)methyloxy-2-fluorophenyl]-4,5,6,7-tetrahydro-2H-indazole (compound No. 6);

7) 3-chloro-2-[4-chloro-5-(3-(4-chloro-3-nitrophenyl)-5-methylisoxazolin-5-yl)methyloxy-2-fluorophenyl]-4,5,6,7-tetrahydro-2H-indazole (compound No. 7);

8) 3-chloro-2-[4-chloro-5-(3-cyano-5-methylisoxazolin-5-yl)methyloxy-2-fluorophenyl]-4,5,6,7-tetrahydro-2H-indazole (compound No. 8);

9) 3-chloro-2-[4-chloro-5-(3-(4-trifluoromethylphenyl)-5-methylisoxazolin-5-yl)methyloxy-2-fluorophenyl]-4,5,6,7-tetrahydro-2H-indazole (compound No. 9);

10) 3-chloro-2-[4-chloro-5-(3-(4-bromophenyl)-5-methylisoxazolin-5-yl)methyloxy-2-fluorophenyl]-4,5,6,7-tetrahydro-2H-indazole (compound No. 10);

11) 3-chloro-2-[4-chloro-5-(3-(4-methoxyphenyl)-5-methylisoxazolin-5-yl)methyloxy-2-fluorophenyl]-4,5,6,7-tetrahydro-2H-indazole (compound No. 11); and 12) 3-chloro-2-[4-chloro-5-(3-(2-chlorophenyl)-5-methylisoxazolin-5-yl)methyloxy-2-fluorophenyl]-4,5,6,7-tetrahydro-2H-indazole (compound No. 12).

In addition, the present invention provides a preparation method of 2-(5-isoxazolinylmethyloxy-phenyl)-4,5,6,7-tetrahydro-2H-indazole derivatives of the formula 1.

The preferred process is described hereinafter in detail.

2-(5-Isoxazolinylmethyloxyphenyl)-4,5,6,7-tetrahydro-2H-indazole derivatives of the formula 1 can be prepared by reacting the compound of formula (II) and nitrile oxide (or a precursor of nitrile oxide) by the 1,3-dipolar cycloaddition reaction (see Scheme 1).

SCHEME 1

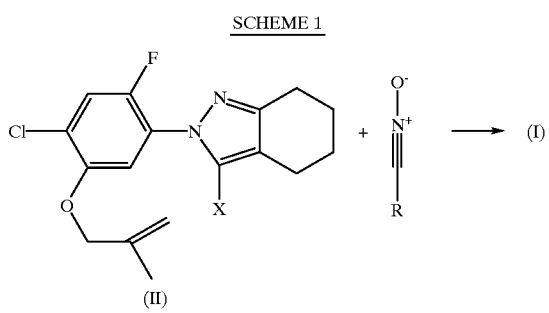

Wherein, X and R are defined as the formula 1.

At this time, a variety of solvents may be used including dichloromethane, tetrahydrofuran, benzene, diethyl ether, alcohol of $C_1$–$C_4$, etc. Preferably anhydrous solvent may be used.

The compound of formula (II) can be prepared by reacting the compound of formula (III) and methallyl chloride or methallyl bromide in the presence of a base by the substitution reaction (see Scheme 2)

SCHEME 2

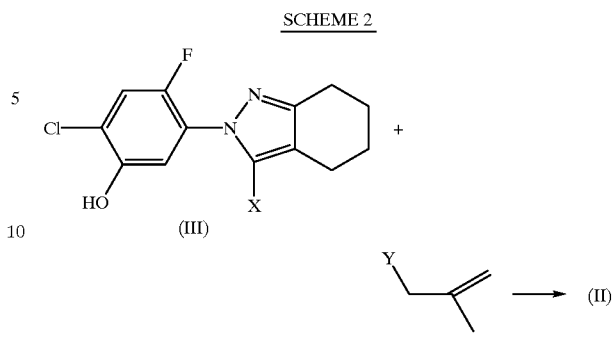

Wherein, X is defined as the formula 1 and Y is a halogen atom.

At this time, the base may be preferably used including sodium hydride, potassium carbonate, etc. A variety of solvents may be used including N,N-dimethylformamide, N,N-dimethylacetamide, tetrahydrofuran, acetone, etc. depending on the base.

The compound of formula (III) can be prepared by the method disclosed by GB Pat. No. 2,127,410 A, but should not be considered to be limited thereto. The compound of formula (III) can be synthesized by other methods.

The preparation method of compounds according to the present invention can be abstracted into the following steps:

1) reacting the compound of formula (III) and methallyl chloride or methallyl bromide in the presence of a base to give a compound of formula (II) by the substitution reaction (step 1); and 2) reacting the compound of formula (II) prepared in the step 1 and nitrile oxide (or a precursor of nitrile oxide) to give the compound of formula 1 by the 1,3-dipolar cycloaddition reaction (step 2).

The present invention also provides herbicidal compositions comprising one or more compounds of 2-(5-isoxazolinylmethyloxyphenyl)-4,5,6,7-tetrahydro-2H-indazole derivatives as an active ingredient.

The compounds of formula 1 have good herbicidal activity particularly in paddy field, and good safety on both seeded rice and transferred rice, particularly transferred rice. It has been found that the compounds are potent herbicides for the control of paddy weeds, for example, ECHOR (*Echinochloa crus-galli* var. oryzicola), SCPJU (*Scirpus juncoides* ROXB.), MOOVA (*Monochoria vaginalis* PRESL.), CYPSE (*Cyperus serotinus* ROTTB.), and SAGPY (*Sagittaria pygmaea* MIQ.), especially for ECHOR, MOOVA and CYPSE. Therefore the compound of the present invention are useful as herbicides, particularly for controling undesired weeds in paddy field.

In addition, novel 2-(5-isoxazolinylmethyl-oxyphenyl)-4,5,6,7-tetrahydro-2H-indazole derivatives of the formula 1 according to the present invention have strong herbicidal activity against paddy weeds comprising ECHOR, SCPJU, MOOVA, CYPSE, and SAGPY with a strong safety on paddy rice, and selectivity among rice and weeds compare to known herbicides; therefore, the compounds of the present invention are very useful as herbicides to kill weeds in cultivating rice.

Also the compounds of the present invention can be used as plant-growth regulators.

Though the compound of formula 1 according to the present invention can be used directly in order to control paddy weeds, it is used mostly in the form of formulation for convenience and stability. The type of formulation can be modified depending on the purpose.

The herbicidal compositions comprising the compounds of this invention can be formulated in forms such as wettable powder, emulsifiable concentrates, granules, dustable powder, soluble liquid, wettable granules, water dispersible granules, etc.

The herbicidal compositions are preferred to comprise one or more active compounds of the present invention with solid or liquid carriers in formulation.

Preferred carriers which are employed in the compositions according to the present invention are solid carriers which are selected from inorganic powders such as kaolin, bentonite, montmorillonite, talc, diatom earth, mica, gypsum, calcium carbonate, apatite, silicon hydroxide, etc.; vegetable powders such as soybean flour, wheat flour, sawdust, tabacco powder, starch powder, crystallized cellulose, etc.; polymers such as petroleum resin, vinylchloride resin, ketone resin, etc.; alumina; and beeswax, and liquid carriers which are selected from alcohols such as methanol, ethanol, benzyl alcohol, etc.; aromatic hydrocarbons such as toluene, benzene, xylene, methyl naphthalene, etc.; halogenated hydrocarbons such as chloroform, carbon tetrachloride, chlorobenzene, etc.; ethers such as 1,4-dioxane, tetrahydrofuran, etc.; ketones such as acetone, methyl ethyl ketone, cyclohexanone, etc.; esters such as ethyl acetate, butyl acetate, ethyleneglycol acetate, etc.; amides such as N,N-dimethylformamide; nitriles such as acetonitrile; ether alcohols such as ethylene glycol, diethyl ether, etc.; and water.

In addition, the herbicidal compositions of the present invention may comprise anionic, cationic or nonionic surfactants in formulation.

The cationic surfactants include long chain alkylammonium salts such as cetyltrimethylammonium bromide salt.

The anionic surfactants include alkali metal, alkali earth metal and ammonium salts comprising alkylarylsulfonic acids such as dodecylbenzenesulfonic acid; alkyloxysulfonic acids such as lauryloxysulfonic acid; arylsulfonic acids such as ligninsulfonic acid, naphthalenesulfonic acid, dibutyl naphthalenesulfonic acid, etc.; laurylether sulfate; aliphatic alcohol sulfate; aliphatic acid; and glycol ether.

The nonionic surfactants include aliphatic alcohols such as oleyl alcohol or cetyl alcohol; caster oil containing phenol, alkylphenol, ethylene oxide or propylene oxide; and the condensation products of either naphthalene or naphthalenesulfonic acid with either phenol or formaldehyde.

The content of the compounds represented by the above formula 1, while varying depending on the formulations, is preferably 1–50 wt % for wetting agents, granules or emulsifyiable concentrates, and 2–40 wt % for soluble liquids or wettable granules.

The application amount of compounds of the foregoing formula 1 is preferably 0.01–4.0 kg per hectare (kg/ha).

In addition, the herbicidal compositions of the present invention can be employed in combination with one or more additional known insecticides, fungicides, vermicides, plant-growth regulators, fertilizers, other agricultural chemicals or other herbicides to improve the herbicidal activity, to broaden the herbicidal spectrum and to achieve synergic effects, if necessary. Examples of useful complementary herbicides include 3-isopropyl-1H-2,1,3-benzothiadiazin-4(3H)one-2,2-dioxide (bentazone), N-(heteroarylaminocarbonyl)-benzenesulfonamides such as methyl 2-[3-(4,6-dimethoxypyrimidin-2-yl)ureidosulfonylmethyl]benzoate (Bensulfuron-methyl), ethyl 5-[3-(4,6-dimethoxypyrimidin-2-yl)ureidosufonyl]-1-methylpyrazole-4-carboxylate (Pyrazosulfuron-ethyl), etc.

Practically and presently preferred embodiments of the present invention are illustrative as shown in the following examples.

However, it will be appreciated that those skilled in the art, on consideration of this disclosure, may make modification and improvements within the sprit and scope of the present invention.

EXAMPLES

Example 1

Preparation of 3-chloro-2-[4-chloro-5-(3-phenyl-5-methylisoxazolin-5-yl)methyloxy-2-fluorophenyl]-4,5,6,7-tetrahydro-2H-indazole (Step 1) Preparation of 3-chloro-2-[4-chloro-5-methallyloxy-2-fluorophenyl]-4,5,6,7-tetrahydro-2H-indazole A mixture of 3-chloro-2-[4-chloro-5-hydroxy-2-fluorophenyl]-4,5,6,7-tetrahydro-2H-indazole (III) (3.0 g, 0.01 mmol), methallylchloride (1.2 g, 0.01 mmol), potassium carbonate (1.8 g, 0.01 mmol) and catalytic amount of potassium iodide in acetone was refluxed for 12 hours. The reaction mixture was cooled to room temperature, filtered and distilled under reduced pressure to remove solvent. The residue was collected and purified by silicagel column chromatography (ethyl acetate:n-hexane=1:3) to afford 3.1 g of the desired compound (yield: 88%).

$^1$H NMR (CDCl$_3$): δ 7.28 (1H, d, J=9.2 Hz), 6.98 (1H, d, J=6.5 Hz), 5.14 (1H, m), 5.01 (1H, m), 4.47 (2H, brs), 2.70 (2H, m), 2.50 (2H, m), 1.85–1.71 (4H, m), 1.84 (3H, s).

MS m/z (relative intensity): 356 (14.5), 355 (7.0), 354 (22.4), 319 (7.2), 299 (3.2), 273 (2.7), 265 (2.2), 198 (4.1), 163 (7.9), 157 (9.4), 55 (100).

(Step 2) Preparation of 3-chloro-2-[4-chloro-5-(3-phenyl-5-methylisoxazolin-5-yl)methyloxy-2-fluorophenyl]-4,5,6,7-tetrahydro-2H-indazole (compound No. 1, R=phenyl, X=chlorine)

3-Chloro-2-[4-chloro-5-methallyloxy-2-fluorophenyl]-4,5,6,7-tetrahydro-2H-indazole (II) (0.3 g, 0.85 mmol) and benzohydroxymoyl chloride (0.16 g, 1.0 mmol) were dissolved in dichloromethane. To the mixture was added triethylamine (0.1 g, 1.0 mmol) and the mixture was stirred for 12 hours at room temperature. The reaction mixture was poured into an ice water and extracted with dichloromethane. The organic layer was washed with brine, dried over anhydrous magnesium sulfate and distilled under reduced pressure. The residue was collected and purified by silica-gel column chromatography (ethyl acetate:n-hexane=1:3) to afford 0.25 g of 3-chloro-2-[4-chloro-5-(3-phenyl-5-methylisoxazolin-5-yl)methyloxy-2-fluorophenyl]-4,5,6,7-tetrahydro-2H-indazole (yield:63%).

$^1$H NMR (CDCl$_3$): δ 7.78–7.39 (5H,m), 7.26 (1H, d, J=9.4 Hz), 7.01 (1H, d, J=6.3 Hz), 4.09 (1H, d, J=9.4 Hz), 3.99 (1H, d, J=9.4 Hz), 3.61 (1H, d, J=16.7 Hz), 3.17 (1H, d, J=16.7 Hz), 2.69 (2H, m), 2.49 (2H, m), 1.90–1.59 (4H, m), 1.64 (3H, s).

MS m/z (relative intensity): 475 (3.2), 474 (2.5), 473 (6.5), 315 (25.2), 313 (31.0), 285 (5.5), 284 (5.3), 220 (2.4), 174 (10.1), 160 (14.1), 146 (3.7), 118 (100), 104 (17.0), 91 (10.5), 77 (37.5).

Example 2–12

Other compounds of the Example 2–8 were prepared by the similar method of the Example 1 given the above.

TABLE 1

| comp. No. | X | R | $^1$H NMR (CDCl$_3$): δ |
|---|---|---|---|
| 1 | Cl | phenyl | 7.78-7.39(5H, m), 7.26(1H, d, J=9.4Hz), 7.01(1H, d, J=6.3 Hz), 4.09(1H, d, J=9.4Hz), 3.99(1H, d, J=9.4Hz), 3.61 (1H, d, J=16.7Hz), 3.17(1H, d, J=16.7Hz), 2.69(2H, m), 2.49(2H, m), 1.90-1.59(4H, m), 1.64(3H, s). |
| 2 | Cl | 4-cyano-phenyl | 7.77(2H, d, J=8.5Hz), 7.68 (2H, d, J=8.5Hz), 7.26(1H, d, J=9.4Hz), 7.00(1H, d, J=6.5Hz), 4.11(1H, d, J=9.4 Hz), 3.99(1H, d, J=9.4Hz), 3.61(1H, d, J=16.7Hz), 3.15 (1H, d, J=16.7Hz), 2.69 (2H, m), 2.49(2H, m), 1.90-1.71(4H, m), 1.64(3H, s). |
| 3 | Cl | 4-methyl-phenyl | 7.59-7.00(6H, m), 4.07 (1H, d, J=9.4Hz), 3.98(1H, d, J=9.4Hz), 3.56(1H, d, J=16.9Hz), 3.13(1H, d, J=16.9Hz), 2.70(2H, m), 2.49(2H, m), 1.85-1.69 (4H, m), 1.61(3H, s). |
| 4 | Cl | 2-fluoro-phenyl | 7.90-6.99(6H, m), 4.10 (1H, d, J=9.4Hz), 3.98(1H, d, J=9.4Hz), 3.69(1H, d, J=16.7Hz), 3.33(1H, d, J=16.7Hz), 2.70(2H, m), 2.50(2H, m), 1.83-1.69 (4H, m), 1.63(3H, s). |
| 5 | Cl | 2,4-dichloro-phenyl | 7.74-7.45(3H, m), 7.27 (1H, d, J=9.2Hz), 7.00(1H, d, J=6.5Hz), 4.10(1H, d, J=9.4Hz), 4.00(1H, d, J=9.4 Hz), 3.55(1H, d, J=16.7Hz), 3.09(1H, d, J=16.7Hz), 2.70 (2H, m), 2.50(2H, m), 1.83-1.54(4H, m), 1.64(3H, s). |
| 6 | Cl | 2-nitro-phenyl | 8.27(2H, d, J=2.0Hz), 7.86 (2H, d, J=2.0Hz), 7.26(1H, d, J=9.2Hz), 7.02(1H, d, J=6.5 Hz), 4.14(1H, d, J=9.4 Hz), 4.00(1H, d, J=9.4Hz), 3.66(1H, d, J=16.5Hz), 3.19 (1H, d, J=16.5Hz), 2.70(2H, m), 2.50(2H, m), 1.83-1.61 (4H, m), 1.66(3H, s). |
| 7 | Cl | 4-chloro-3-nitro-phenyl | 8.10(1H, d, J=2.0Hz), 7.87 (1H, dd, J=8.5, 2.0Hz), 7.60 (1H, d, J=8.5Hz), 7.27(1H, d, J=9Hz), 7.02(1H, d, J=6.5 Hz), 4.13(1H, d, J=9.6Hz), 4.00(1H, d, J=9.6Hz), 3.64 (1H, d, J=16.7Hz), 3.17(1H, d, J=16.7Hz), 2.69(2H, m), 2.50(2H, m), 1.91-1.68(4H, m), 1.65(3H, s). |
| 8 | Cl | cyano | 7.31(1H, d, J=9Hz), 6.98(1H, d, J=6.5Hz), 4.12(1H, d, J=9.7Hz), 3.96(1H, d, J=9.7 Hz), 3.51(1H, d, J=17.2Hz), 2.98(1H, d, J=17.2Hz), 2.70 (2H, m), 2.51(2H, m), 1.85-1.53(4H, m), 1.60(3H, s). |
| 9 | Cl | 4-tri-fluoro-methyl-phenyl | 7.77(2H, d, J=8.2Hz), 7.65 (2H, d, J=8.2Hz), 7.26(1H, d, J=6.5Hz), 7.00(1H, d, J=6.5Hz), 4.10(1H, d, J=9.4 Hz), 3.98(1H, d, J=9.4Hz), 3.61(1H, d, J=16.7Hz), 3.16 (1H, d, J=16.7Hz), 2.69(2H, m), 2.49(2H, m), 1.90-1.71 (4H, m), 1.64(3H, s). |
| 10 | Cl | 4-bromo-phenyl | 7.82-7.22(5H, m), 7.01(1H, d, J=6.3Hz), 4.09(1H, d, J=9.4Hz), 3.99(1H, d, J=9.4 Hz), 3.58(1H, d, J=16.7Hz), 3.14(1H, d, J=16.7Hz), 2.69 (2H, m), 2.50(2H, m), 1.83-1.71(4H, m), 1.63(3H, s). |
| 11 | Cl | 4-methoxy-phenyl | 7.60(2H, d, J=9.0Hz), 7.26 (1H, d, J=9.2Hz), 7.01(1H, d, J=6.5Hz), 6.91(2H, d, J=9.0Hz), 4.11(1H, d, J=9.4 Hz), 3.99(1H, d, J=9.4Hz), 3.84(3H, s), 3.57(1H, d, J=16.7Hz), 3.14(1H, d, J=16.7Hz), 2.69(2H, m), 2.50 (2H, m), 1.90-1.71(4H, m), 1.63(3H, s). |
| 12 | Cl | 2-chloro-phenyl | 7.64-7.25(6H, m), 7.03(1H, d, J=6.7Hz), 4.13(1H, d, J=9.4Hz), 4.01(1H, d, J=9.4 Hz), 3.74(1H, d, J=17.1Hz), 3.36(1H, d, J=17.1Hz), 2.71 (2H, m), 2.51(2H, m), 1.83-1.69(4H, m), 1.65(3H, s) |

The herbicidal activity of compounds of the above formula 1 is demonstrated in a greenhouse and a typical test example is given below.

Experimental Example

Herbicidal Test Against ECHOR and ORYSA

A plastic pot having a surface area of 140 cm$^2$ was filled with puddled sandy loam soil containing 1.2% organic matter (pH 6). Rice seedlings at the 2–2.5 leaf stage (ORYSA, *Oryza sativa* L.; common name is rice) and pregeminated seeds of rice were transplanted or seeded at the depth of 2 cm, respectively. Then the seeds of ECHOR, SCPJU, MOOVA, CYPSE and SAGPY were seeded in the same pot, wherein the pot was watered at the depth of 3 cm just after planting.

A solution of the test compound and a nonionic surfactant (Tween-20) in 50% aqueous acetone was poured into water. When the test compound was insoluble in the above solvent system, it was formulated as a wettable powder. The concentration of the test compound or wettable powder in solution may be varied to give a range of application rates, preferably 4.0 kg/ha or less. Two days after planting, this solution was apllied to the pot.

Two to three weeks after the application of the herbicide, the herbicidal activity on paddy weeds and the phytotoxicity to the paddy rice plant were visually rated by a percentage grading wherein 0 signifies no herbicidal activity and 100 signifies complete kill. The results are shown in the following table 2.

In the Table 2, the compound marked as F2 was prepared according to GB Pat. No. 2,127,410 A in order to compare the herbicidal activity as a Reference, whose structure is represented by the formula 2.

Formula 2

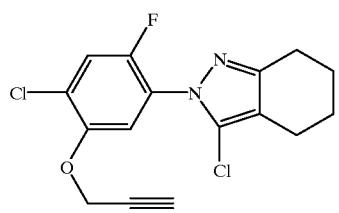

TABLE 2

| comp. No. | Rate (kg/ha) | ORYSA (3 leaf) | ORYSA (seed) | A | B | C | D | E |
|---|---|---|---|---|---|---|---|---|
| 1 | 4.0 | 20 | 100 | 100 | 80 | 100 | 100 | 90 |
|   | 1.0 | 20 | 100 | 100 | 70 | 100 | 100 | 80 |
|   | 0.25 | 10 | 100 | 100 | 70 | 100 | 100 | 70 |
|   | 0.063 | 0 | 80 | 100 | 60 | 100 | 100 | 50 |
|   | 0.016 | 0 | 50 | 100 | 40 | 100 | 100 | 40 |
| 2 | 4.0 | 40 | 100 | 100 | 30 | 100 | 100 | 100 |
|   | 1.0 | 0 | 70 | 100 | 20 | 100 | 100 | 40 |
|   | 0.25 | 0 | 50 | 100 | 10 | 100 | 70 | 70 |
|   | 0.063 | 0 | 10 | 100 | 10 | 70 | 50 | 20 |
|   | 0.016 | 0 | 0 | 95 | 0 | 60 | 0 | 10 |
| 3 | 4.0 | 30 | 100 | 100 | 70 | 100 | 100 | 100 |
|   | 1.0 | 10 | 100 | 100 | 60 | 100 | 100 | 100 |
|   | 0.25 | 10 | 70 | 100 | 50 | 100 | 100 | 50 |
|   | 0.063 | 0 | 60 | 100 | 50 | 100 | 100 | 50 |
|   | 0.016 | 0 | 50 | 100 | 40 | 90 | 90 | 0 |
| 4 | 4.0 | 30 | 100 | 100 | 90 | 100 | 100 | 100 |
|   | 1.00 | 30 | 100 | 100 | 80 | 100 | 100 | 90 |
|   | 0.25 | 10 | 100 | 100 | 60 | 100 | 100 | 80 |
|   | 0.063 | 0 | 50 | 100 | 70 | 100 | 100 | 50 |
|   | 0.016 | 0 | 40 | 100 | 40 | 80 | 0 | 30 |
| 5 | 4.0 | 20 | 100 | 100 | 80 | 100 | 100 | 100 |
|   | 1.0 | 10 | 100 | 100 | 60 | 100 | 100 | 100 |
|   | 0.25 | 0 | 100 | 100 | 50 | 100 | 100 | 60 |
|   | 0.063 | 0 | 40 | 100 | 30 | 100 | 100 | 40 |
|   | 0.016 | 0 | 20 | 80 | 0 | 95 | 100 | 0 |
| 6 | 4.0 | 20 | 100 | 100 | 70 | 100 | 100 | 100 |
|   | 1.0 | 10 | 70 | 100 | 60 | 100 | 100 | 60 |
|   | 0.25 | 0 | 20 | 100 | 40 | 100 | 100 | 20 |
|   | 0.063 | 0 | 20 | 97 | 30 | 98 | 100 | 20 |
|   | 0.016 | 0 | 10 | 70 | 0 | 90 | 0 | 0 |
| 7 | 4.0 | 30 | 95 | 100 | 70 | 100 | 100 | 100 |
|   | 1.0 | 0 | 85 | 100 | 70 | 100 | 100 | 100 |
|   | 0.25 | 0 | 60 | 100 | 40 | 100 | 100 | 50 |
|   | 0.063 | 0 | 30 | 100 | 40 | 100 | 100 | 30 |
|   | 0.016 | 0 | 10 | 100 | 10 | 100 | 100 | 0 |
| 8 | 4.0 | 45 | 100 | 100 | 100 | 100 | X | 100 |
|   | 1.0 | 40 | 100 | 100 | 90 | 100 | X | 100 |
|   | 0.25 | 30 | 100 | 100 | 80 | 100 | X | 100 |
|   | 0.063 | 20 | 100 | 100 | 80 | 100 | X | 100 |
|   | 0.016 | 10 | 100 | 100 | 20 | 100 | X | 50 |
| 9 | 4.0 | 10 | 100 | 100 | 80 | 100 | 100 | 100 |
|   | 1.0 | 0 | 100 | 100 | 50 | 100 | 100 | 100 |
|   | 0.25 | 0 | 100 | 100 | 40 | 100 | 100 | 0 |
|   | 0.063 | 0 | 50 | 80 | 30 | 100 | 100 | 0 |
|   | 0.016 | 0 | 30 | 30 | 20 | 70 | 0 | 0 |
| 11 | 4.0 | 50 | 100 | 100 | 70 | 100 | 100 | 100 |
|   | 1.0 | 20 | 100 | 100 | 60 | 100 | 100 | 100 |
|   | 0.25 | 0 | 100 | 100 | 50 | 100 | 100 | 100 |
|   | 0.063 | 0 | 100 | 100 | 30 | 100 | 100 | 20 |
|   | 0.016 | 0 | 50 | 100 | 20 | 100 | 80 | 0 |
| 12 | 4.0 | 20 | 100 | 100 | 100 | 100 | 100 | 100 |
|   | 1.0 | 20 | 100 | 100 | 100 | 100 | 100 | 100 |
|   | 0.25 | 20 | 100 | 100 | 100 | 100 | 100 | 50 |
|   | 0.063 | 20 | 100 | 100 | 100 | 100 | 100 | 30 |
|   | 0.016 | 0 | 40 | 60 | 40 | 100 | 100 | 10 |

TABLE 2-continued

| comp. No. | Rate (kg/ha) | ORYSA (3 leaf) | ORYSA (seed) | A | B | C | D | E |
|---|---|---|---|---|---|---|---|---|
| F2 | 4.0 | 100 | 100 | 100 | 100 | 100 | 90 | 100 |
|   | 1.0 | 70 | 100 | 100 | 100 | 100 | 90 | 100 |
|   | 0.25 | 60 | 100 | 100 | 100 | 100 | 90 | 100 |
|   | 0.063 | 40 | 100 | 100 | 80 | 100 | 40 | 90 |
|   | 0.016 | 20 | 100 | 100 | 70 | 100 | 0 | 30 |

A: ECHOR
B: SCPJU
C: MOOVA
D: CYPSE
E: SAGPY
F2: The compound of formula 2
X: Not determined As shown in the above results, 2-(5-Isoxazolinylmethyloxyphenyl)-4,5,6,7-tetrahydro-2H-indazole derivatives of the present invention have shown the excellent herbicidal activity, particulary the improved selectivity, compared with the compound which has been already used as a herbicide.

Even in low concentration, the compounds represented by the formula 1 according to the present invention, used at 4 kg/ha or less, have shown an excellent level of herbicidal activity, together with crop tolerance on the weeds used in the foregoing experiments.

What is claimed is:

1. 2-(5-Isoxazolinylmethyloxyphenyl)-4,5,6,7-tetrahydro-2H-indazole derivatives of the formula 1:

(I)

Formula 1

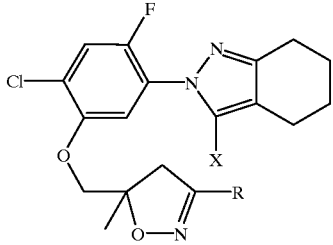

wherein,

X represents a chlorine atom or a hydroxy group;

R represents an alkyl group of $C_1$–$C_5$, a substituted or unsubstituted phenyl group, a cyano group, a carboxyl group, a carboxyl ester group, or a substituted or unsubstituted heterocyclic ring; and in case of a phenyl group or a heterocyclic ring being substituted, the phenyl group or the heterocyclic ring is optionally substituted by one or more identical or different substituents selected from the group consisting of alkyl groups of $C_1$–$C_3$, alkoxy groups of $C_1$–$C_3$, halogen atoms, cyano groups, nitro groups, carboxyl groups and carboxyl ester groups.

2. The 2-(5-isoxazolinylmethyloxyphenyl)-4,5,6,7-tetrahydro-2H-indazole derivatives according to claim 1, wherein R is a substituted or unsubstituted phenyl group or a substituted or unsubstituted heterocyclic ring, or a cyano group.

3. The 2-(5-isoxazolinylmethyloxyphenyl)-4,5,6,7-tetrahydro-2H-indazole derivatives according to claim 1, wherein the compound of the formula 1 is selected from the group consisting of:

1) 3-chloro-2-[4-chloro-5-(3-phenyl-5-methylisoxazolin-5-yl)methyloxy-2-fluorophenyl]-4,5,6,7-tetrahydro-2H-indazole;
2) 3-chloro-2-[4-chloro-5-(3-(4-cyanophenyl)-5-methylisoxazolin-5-yl)methyloxy-2-fluorophenyl]-4,5,6,7-tetrahydro-2H-indazole;
3) 3-chloro-2-[4-chloro-5-(3-(4-methylphenyl)-5-methylisoxazolin-5-yl)methyloxy-2-fluorophenyl]-4,5,6,7-tetrahydro-2H-indazole;
4) 3-chloro-2-[4-chloro-5-(3-(2-fluorophenyl)-5-methylisoxazolin-5-yl)methyloxy-2-fluorophenyl]-4,5,6,7-tetrahydro-2H-indazole;
5) 3-chloro-2-[4-chloro-5-(3-(2,4-dichlorophenyl)-5-methylisoxazolin-5-yl)methyloxy-2-fluorophenyl]-4,5,6,7-tetrahydro-2H-indazole;
6) 3-chloro-2-[4-chloro-5-(3-(2-nitrophenyl)-5-methylisoxazolin-5-yl)methyloxy-2-fluorophenyl]-4,5,6,7-tetrahydro-2H-indazole;
7) 3-chloro-2-[4-chloro-5-(3-(4-chloro-3-nitrophenyl)-5-methylisoxazolin-5-yl)methyloxy-2-fluorophenyl]-4,5,6,7-tetrahydro-2H-indazole;
8) 3-chloro-2-[4-chloro-5-(3-cyano-5-methylisoxazolin-5-yl)methyloxy-2-fluorophenyl]-4,5,6,7-tetrahydro-2H-indazole;
9) 3-chloro-2-[4-chloro-5-(3-(4-trifluoromethylphenyl)-5-methylisoxazolin-5-yl)methyloxy-2-fluorophenyl]-4,5,6,7-tetrahydro-2H-indazole (compound No. 9);
10) 3-chloro-2-[4-chloro-5-(3-(4-bromophenyl)-5-methylisoxazolin-5-yl)methyloxy-2-fluorophenyl]-4,5,6,7-tetrahydro-2H-indazole (compound No. 10);
11) 3-chloro-2-[4-chloro-5-(3-(4-methoxyphenyl)-5-methylisoxazolin-5-yl)methyloxy-2-fluorophenyl]-4,5,6,7-tetrahydro-2H-indazole (compound No. 11); and
12) 3-chloro-2-[4-chloro-5-(3-(2-chlorophenyl)-5-methylisoxazolin-5-yl)methyloxy-2-fluorophenyl]-4,5,6,7-tetrahydro-2H-indazole.

4. A process for preparation of 2-(5-isoxazolinylmethyloxyphenyl)-4,5,6,7-tetrahydro-2H-indazole derivatives of claim 1 which comprises the steps of:

1) reacting the compound of formula (III) and methallyl chloride or methallyl bromide in the presence of a base to give a compound of formula (II) by the substitution reaction (step 1); and
2) reacting the compound of formula (II) prepared in the step 1 and nitrile oxide (or a precursor of nitrile oxide) to give the compound of formula 1 by the 1,3-dipolarcycloaddition reaction (step 2)

SCHEME 1

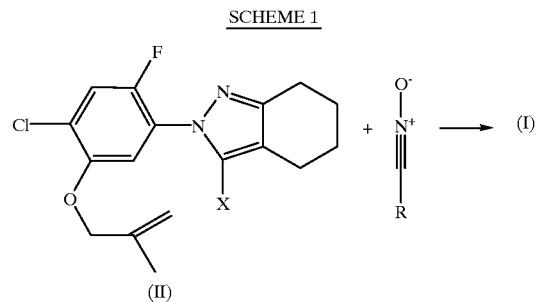

SCHEME 2

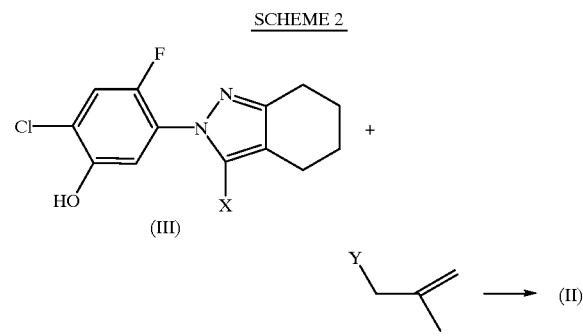

Wherein X and R are defined as the formula 1 respectively, and Y represents a halogen atom.

5. Herbicidal compositions comprising one or more compounds of 2-(5-isoxazolinylmethyloxyphenyl)-4,5,6,7-tetrahydro-2H-indazole derivatives of claim 1 as an active ingredient.

6. The herbicidal compositions according to claim 5, characterized in controlling paddy weeds comprising ECHOR (*Echinochloa crus-galli* var. oryzicola), SCPJU (*Scirpus juncoides* ROXB.), MOOVA (*Monochoria vaginalis* PRESL.), CYPSE (*Cyperus serotinus* ROTTB.), and SAGPY (*Sagittaria pygmaea* MIQ.).

7. The herbicidal compositions according to claim 5, comprising insecticides, fungicides, vermicides, plant-growth regulators or fertilizers in addition to the 2-(5-isoxazolinylmethyloxyphenyl)-4,5,6,7-tetrahydro-2H-indazole derivatives of claim 1.

* * * * *